United States Patent [19]

Huebner

[11] Patent Number: 5,263,988
[45] Date of Patent: Nov. 23, 1993

[54] BIPOLAR ENDOPROSTHESIS

[75] Inventor: Randall Huebner, Beaverton, Oreg.

[73] Assignee: Exactech, Inc., Gainesville, Fla.

[21] Appl. No.: 997,658

[22] Filed: Dec. 29, 1992

Related U.S. Application Data

[63] Continuation of Ser. No. 747,512, Aug. 20, 1991, abandoned.

[51] Int. Cl.⁵ .............................. A61F 2/32; A61F 2/36
[52] U.S. Cl. ............................................ 623/22; 623/23
[58] Field of Search ........................ 623/16, 18, 22, 23

[56] References Cited

U.S. PATENT DOCUMENTS

| | | | |
|---|---|---|---|
| 3,818,512 | 6/1974 | Shersher | 623/23 |
| 4,718,911 | 1/1988 | Kenna | 623/22 |
| 4,770,658 | 9/1988 | Geremakis | 623/22 |
| 4,936,855 | 6/1990 | Sherman | 623/22 |
| 5,009,665 | 4/1991 | Serbouser et al. | 623/22 |
| 5,019,105 | 5/1991 | Wiley | 623/22 |
| 5,062,853 | 11/1991 | Forte | 623/22 |
| 5,092,897 | 3/1992 | Forte | 623/22 |

FOREIGN PATENT DOCUMENTS

2117646 4/1985 United Kingdom ................. 623/22

*Primary Examiner*—Randall L. Green
*Assistant Examiner*—Dinh X. Nguyen
*Attorney, Agent, or Firm*—Spensley Horn Jubas & Lubitz

[57] ABSTRACT

A bipolar endoprosthesis assembly which provides for a wide-range of motion between a bone and a socket (e.g., a femur and an acetabular socket), comprising a metal outer shell element, a ultra-high molecular weight, low-friction insert formed to fit within the shell element, and a locking ring designed to lock the assembly together with a femoral head prosthesis. The outer shell has a generally spherical shape on its outer surface to be received by a human socket such as the acetabulum. The inner surface of the outer shell is faceted to inhibit rotation of a correspondingly shaped inner insert. The insert has an outside surface shaped to mate with the inside surface of the outer shell element. The locking ring is slotted to facilitate insertion of a femoral head prosthesis. The locking ring also has dual sets of locking barbs shaped to mate with recesses on the inner surface of the outer shell element. The redundant locking mechanism of the locking ring inhibits accidental in vivo disassembly of the device yet allows for relatively easy intraoperative disassembly without specialty tools or fixtures.

14 Claims, 6 Drawing Sheets

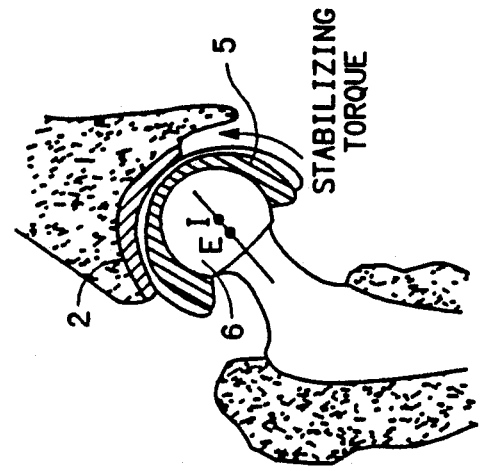
FIG. 2b PRIOR ART POSITIVE ECCENTRICITY "SELF CENTERING"
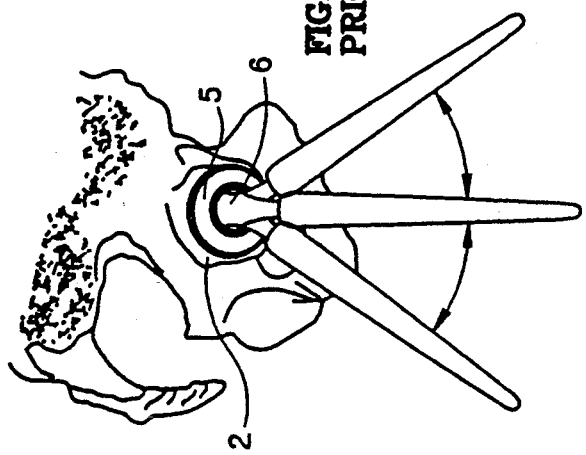
FIG. 2c PRIOR ART ACETABULAR ARTICULATION HIP PROSTHESIS
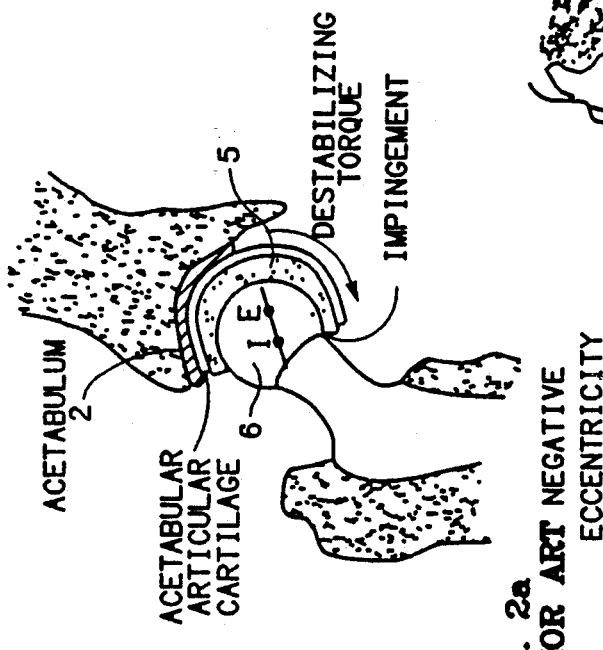
FIG. 2a PRIOR ART NEGATIVE ECCENTRICITY

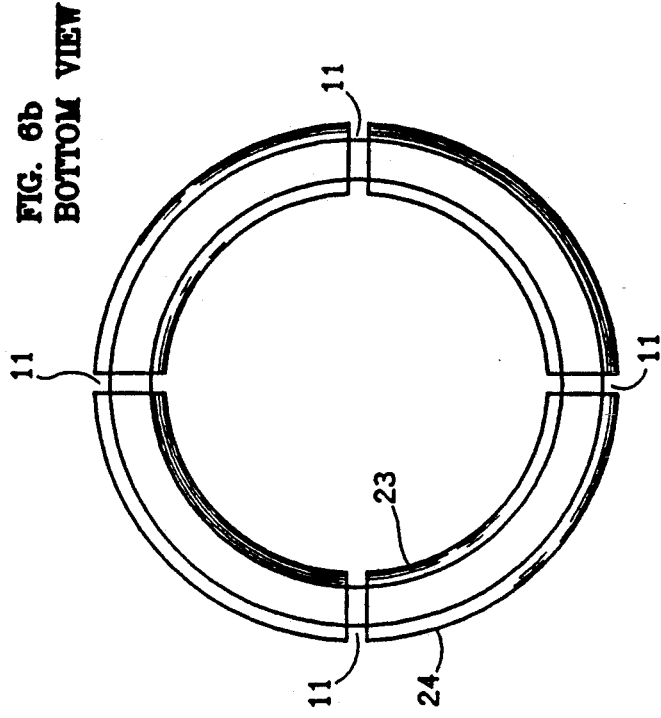
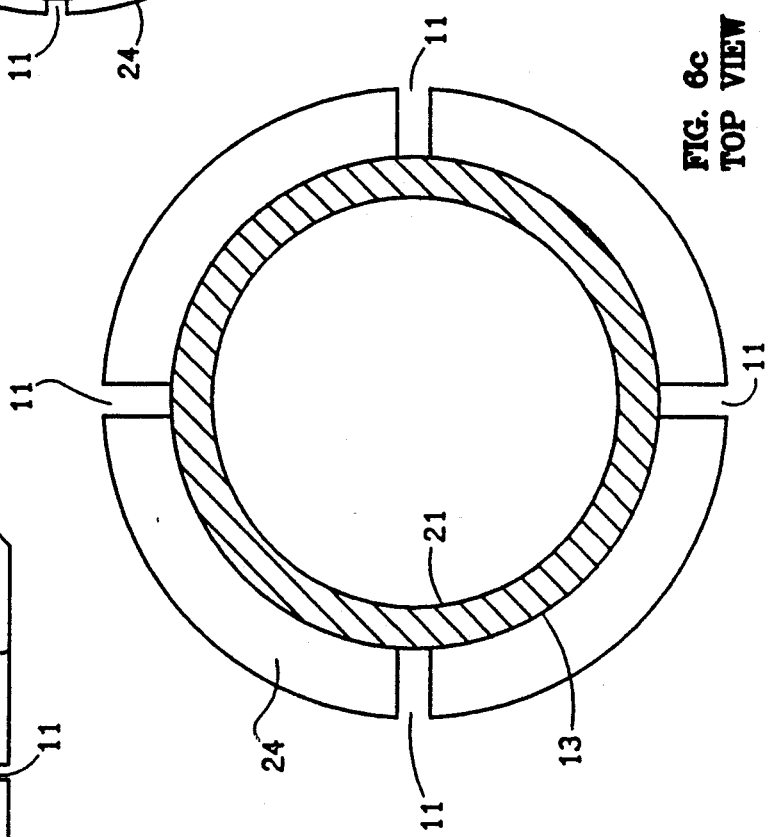
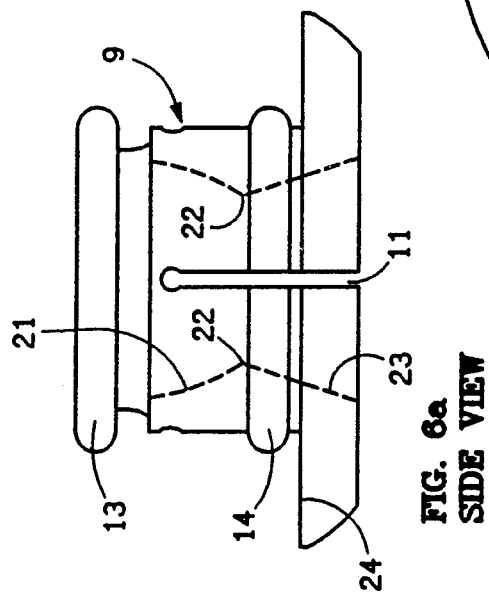

BIPOLAR ENDOPROSTHESIS

This is a continuation of application Ser. No. 07/747,512 filed on Aug. 20, 1991, now abandoned.

BACKGROUND OF INVENTION

1. Field of the Invention

This invention relates to surgically implanted prosthetic devices. More particularly, this invention concerns a dual-locking mechanism bipolar hip prosthesis that allows for articulation between the human acetabulum and the femoral head of a hip replacement prosthesis.

2. Description of Related Art

Acetabular degeneration associated with single component Austin-Moore or Thompson type endoprostheses is well documented. Although these signal component endoprostheses have achieved general acceptance, long-term follow-up results have revealed many problems, including increased acetabulum wear, protrusion, stem loosening, and dislocation. The major complication of increased acetabular wear is believed to be due to high contact stress and excessive friction between the metal femoral head and the natural acetabulum.

Consequently, developers have sought alternative solutions to reduce the friction between prosthesis and acetabulum. This search has produced a number of multi-component femoral bipolar endoprostheses possessing a low-friction joint between a conventional total hip femoral prothesis and a cup component that articulates with the acetabulum. These prosthetic devices fit loosely into the natural acetabulum. They are designed to connect the femoral head and stem prosthesis to the natural acetabulum and to prevent wear of the acetabulum cartilage frequently caused by one-piece total hip prostheses. Because the motion is greater at the inner low-friction prosthesis joint, acetabular articulation and its associated erosion is reduced.

Constructions of this type are shown by way of example in the following U. S. patents:

English, U.S. Pat. No. 4,004,300
D'Errico, U.S. Pat. Nos. 4,044,403 and 4,172,296
Ramos, U.S. Pat. No. 4,380,090
Pappas, U.S. Pat. Nos. 4,624,674 and 4,619,658
Legrand, U.S. Pat. No. 4,676,799
Fichera et al., U.S. Pat. No. 4,714,477
Jurgutis, U.S. Pat. No. 4,728,335
Oh, U.S. Pat. No. 4,770,661

Each of these constructions consists of a cup member having an outer shell for implantation into the skeletal cavity and an inner cavity for receiving a male prosthesis member, usually having a spherical shape. Bipolar endoprostheses possess two distinct characteristics: at least two centers of movement and a smooth outer shell for acetabular articulation.

One of the considerations in designing a bipolar endoprostheses is the relative positioning of the internal (femoral component head to bearing insert) and external (metal cup to acetabulum) centers of articulation. The original prior art bipolar endoprostheses depicted in FIG. 2a were designed with "negative eccentricity" because the external center of articulation (marked "E") was positioned above the internal center of articulation (marked "I").

The configuration resulted in a persistent varus tilt or vertical position of the external acetabular cup, as depicted in FIG. 2a. Negative eccentricity produces a de-stabilizing torque, which reduces internal articulation and provides undesirable load bearing conditions. If the femoral head 6 became impinged against the inner surface of the outer shell, in vivo component separation and disassembly could occur. U.S. Pat. No. 3,813,699 issued to Gilberty and U.S. Pat. No. 4,172,296 issued to D'Errico are examples of bipolar endoprostheses designed with negative eccentricity.

More recently, conscientious efforts have been made to create endoprostheses with "positive eccentricity," possibly because of reports of persistent problems with dislocation at a rate comparable to more conventional endoprostheses. As depicted in FIG. 2b, positive eccentricity occur when the external cup center ("E") of articulation is positioned below the internal articulation center ("I"). This configuration keeps the external metal cup from falling into either a marked varus or valgus position and is called "self-centering." U.S. Pat. Nos. 4,619,658 and 4,634, 674 issued to Pappas et al. are examples of bipolar endoprostheses designed with positive eccentricity.

As depicted in FIG. 2b, self-centering cups produce a stabilizing torque which creates a consistent cup position, decreasing the chance of femoral head impingement. The stabilizing torque provides a symmetric load-bearing surface, increases inner joint motion and decreases acetabular wear. Thus, positive eccentricity is a desired characteristic in a bipolar endoprosthesis design.

Intraoperative considerations such as ease of prosthetic component assembly and disassembly and the nature of the installation and removal instrumentation are important to bipolar endoprosthesis design. A continuing objective in the design of bipolar endoprostheses is to allow ease of intraoperative assembly while simultaneously providing for a substantially locked component to ensure against accidental in vivo disassembly. Many of the prostheses in the prior art can be assembled easily by "popping" the femoral head into the acetabulum component. These designs risk in vivo separation of components if insertion and removal forces are relatively small.

However, if the endoprosthesis is designed such that its components are not easily separated, then a relatively large assembly force is normally required. In addition, an undesirable large disassembly force is required should a surgeon need to change the femoral head or should revision of the component to a total hip arthroplasty with a permanently fixed acetabular component be necessary. The increased assembly and disassembly force adds time-consuming steps to the surgery, makes reduction after a post-operative dislocation more difficult, and increases the potential morbidity and mortality associated with subsequent surgical corrections.

In order to decrease the potential for accidental in vivo disassembly, yet allow for relatively easy intraoperative assembly and disassembly, several designs have been developed which use a bearing component with a means for locking the hip prosthesis ball component into the acetabular shell. U.S. Pat. No. 4,380,090 issued to Ramos is an example of such an endoprosthesis. Ramos teaches a four-piece artificial hip socket consisting of an acetabular shell, a bearing insert, an annular bearing, and a locking ring. Ramos uses a split-ring bearing and an annular spring locking ring to engage the femoral head. Ramos has the disadvantage of having multiple inserts to assemble and keep track of during surgery.

Other designs using locking rings for multiple component designs are disclosed by U.S. Pat. No. 4,619,658 issued to Pappas et al. and U.S. Pat. No. 4,770,661 issued to Oh. The retaining ring disclosed by Pappas performs two functions. First, it holds a split inner bearing subassembly together during prosthesis assembly. Second, it retains the acetabular cup on and over the split bearing insert, preventing separation during joint rotation. However, this structure can at times be too easily disassembled.

The locking ring taught by Oh has an inner annular surface and external threads which are threaded into the acetabular shell. The locking ring utilizes radially extending tabs which are received in a locking groove of the acetabular shell. However, the threaded coupling makes this structure difficult to use during surgery.

Therefore, a prosthesis with relatively easy assembly and disassembly yet capable of producing a substantial locking of prosthetic components is still desired.

In order to remedy the deficiencies of the prior art, it is an object of the present invention to provide a bipolar endoprosthesis which is easily manufactured, has positive eccentricity, and is self-centering. It is also an object of this invention to provide a bipolar endoprosthesis which is quickly and easily assembled and disassembled intraoperatively, and yet provides a substantial locked assembly. Other objects of the present invention are to substantially reduce accidential in vivo disassembly, reduce inventory requirements, and make external reduction possible.

SUMMARY OF THE INVENTION

This invention concerns a bipolar hip prosthesis that allows for articulation between the acetabular cartilage and the femoral head of a total hip replacement prosthesis. The invention accomplishes a reduction in the intraoperative assembly and disassembly force required to insert the femoral head into and remove the femoral head from the bipolar hip prosthesis.

In accordance with these and other objects, the present invention teaches a bipolar endoprosthesis comprising a three-piece sub-assembly. More specifically, the invention provides a ball-and-socket joint prosthesis which comprises an outer shell, a generally hemispherical insert that fits within the outer shell, and a double-locking ring.

The present invention further teaches a locking mechanism which uses the combination of a faceted polyethylene insert and dual sets of locking barbs to achieve better locking integrity of the component assembly. The design is well suited to a "nesting" of internal parts for a series of external parts, which significantly reduces inventories producing a cost effective solution.

In the preferred embodiment of the present invention, the outer shell is preferably made of a hard, polished medical grade metal, such as a cobalt-chromium-molybdenum alloy. The exterior surface of the shell assembly is generally hemispherical and adapted to be received in the acetabulum of the human body. The interior surface of the shell assembly has a faceted face to inhibit the rotation of a correspondingly shaped hemispherical insert. In the preferred embodiment of the present invention, the hemispherical insert is made of a low-friction material, such as a medical grade ultra-high molecular weight polyethylene.

The locking ring is also preferably made of ultra-high molecular weight polyethylene. The locking ring has a conical opening at its throat to accommodate the insertion of a femoral head. The ring is segmented, preferably into four leaves, to facilitate entry of the femoral head by momentarily deforming. With the femoral head in place, the locking ring is pushed into the metal shell. Locking tabs or barbs protruding from two levels of the locking ring engage locking recesses located on the inner surface of the outer metal shell to securely lock the assembly together.

The inventive structure provides a dual locking mechanism for locking the component assembly. Should deformations take place within the hemispherical insert due to loading from the femoral head, the locking ring is pushed up against the locking tabs, forcing the locking tabs more tightly into the locking recesses, which in turn inhibits disassembly of the component. This configuration provides a very substantial locking integrity yet allows for relatively easy intraoperative disassembly.

Further aspects of the present invention will become apparent from the following detailed description when considered in conjunction with the accompanying drawings. It should be understood, however, that the detailed description and the specific examples, while representing the preferred embodiment of the invention, are given by way of illustration only.

DESCRIPTION OF THE DRAWINGS

FIG. 2a is a schematic view illustrating a prior art hip joint bipolar endoprosthesis with negative eccentricity.

FIG. 2b is a schematic view illustrating a prior art hip joint bipolar endoprosthesis with positive eccentricity.

FIG. 2c is a schematic view illustrating the acetabular articulation of a hip joint bipolar endoprosthesis (prior art and present invention).

FIG. 6a is a side plan view of the locking ring used in the preferred embodiment of the present invention.

FIG. 6b is a bottom plan view of the locking ring used in the preferred embodiment of the present invention.

FIG. 6c is a top plan view of the locking ring used in the preferred embodiment of the present invention.

Like reference characters and designations in the drawings refer to like elements.

DETAILED DESCRIPTION OF THE INVENTION

Figure 1:
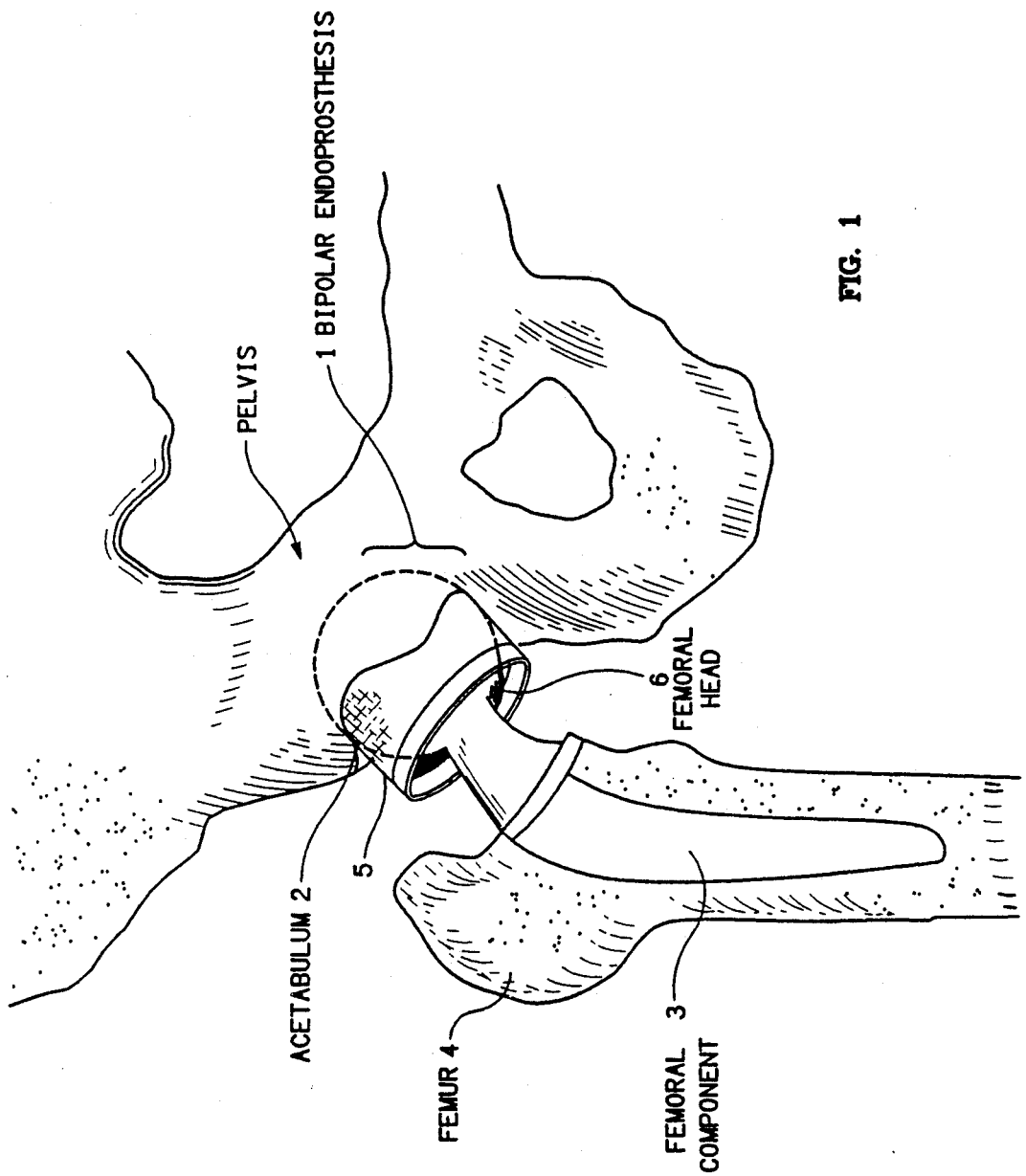
FIG. 1 is a schematic view illustrating a hip joint bipolar endoprosthesis applied to the human body.

The following description is of the best presently contemplated modes of carrying out the invention. FIG. 1 deptics a bipolar endoprosthesis 1 embodying the principles of the present invention implanted into the acetabular socket 2 of the human body. Although the following description is primarily directed to a hip joint prosthesis, it should be emphasized that the scope of this invention includes application in other articulating joints. Therefore, the following description of the bipolar endoprosthesis 1 is for purposes of illustration and should not be construed as a limitation of the present invention.

In use, the present invention is similar in function to the prior art. As depicted in FIG. 1 and FIG. 2, the bipolar endoprosthesis 1 is designed to mate with a femoral insert member 3. The femoral component 3 is adapted to be implanted into the human femur 4 through well-known medical procedures. Similarly, the bipolar endoprosthesis 1 is placed within the acetabular socket 2 using conventional medical and surgical techniques. In the typical procedure, the acetabular socket 2 is worked upon to accommodate the bipolar shell member 5 of the endoprosthesis 1. The bipolar shell member 5 is left unsecured and allowed to freely articulate within the socket 2.

As shown in FIG. 1, the approximately spherical femoral head 6 is inserted and locked into the bipolar endoprosthesis 1, and then the outer shell is placed in the acetabular socket 2. FIG. 2c shows the motion of the femoral insert and related acetabular articulation that occurs during typical use of the hip prosthesis. The exterior surface 7 of the outer shell 5 of the bipolar device articulates within the natural acetabular socket 2 of the human hip. At the same time, the femoral head 6 articulates within the inner bearing insert (not shown). The dual articulation inhibits further decay of the natural acetabular socket 2 frequently caused by total hip prostheses.

STRUCTURE OF THE INVENTION

Figure 3:
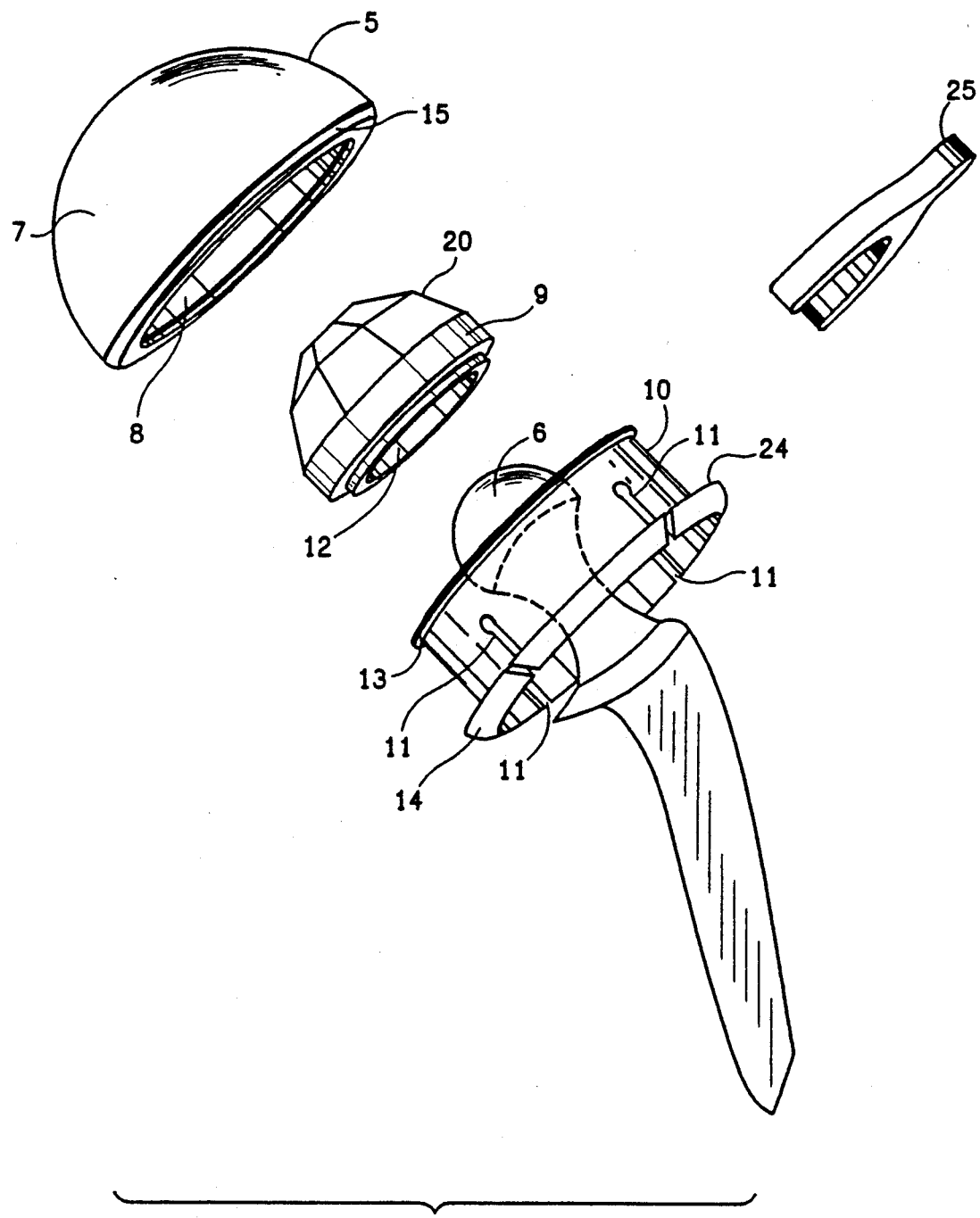
FIG. 3 is an exploded perspective view showing a hip joint bipolar endoprosthesis in accordance with the preferred embodiment of the present invention.

FIG. 3 depicts an exploded view of the preferred embodiment of the present invention. The bipolar endoprosthesis consists of three subassemblies: an outer shell 5, a hemispherical insert 9, and a locking ring 10.

The outer shell 5 preferably is made in a set of selected sizes out of medical grade metal, such as a cobalt-chromium-molybdenum alloy. However, any material that is relatively inert and smooth could be used (e.g., ceramic, plastic, or composite materials). The exterior surface 7 of the shell assembly 5 is generally highly polished, hemispherical, and adapted to be received in a natural socket of a joint. A least part of the interior surface 8 of the shell assembly has a faceted face to inhibit the rotation of the correspondingly-shaped hemispherical insert 9. In the preferred embodiment of the present invention, the hemispherical insert 9 is made of a low-friction material such as a medical grade ultra-high molecular weight polyethylene. However, any material that is relatively inert, low friction, and smooth could be used (e.g., ceramic, composite material, or non-galling metal alloys). The interior surface 12 of the insert 9 has a smooth hemispherical face to allow articulation with the femoral head 6. The interior of the insert 9 is matched in size to the femoral head 6. The bipolar subassemblies are locked together with the femoral prosthesis using the locking ring 10. The locking ring 10 preferably is also made of ultra-high molecular weight polyethylene.

Figure 4:
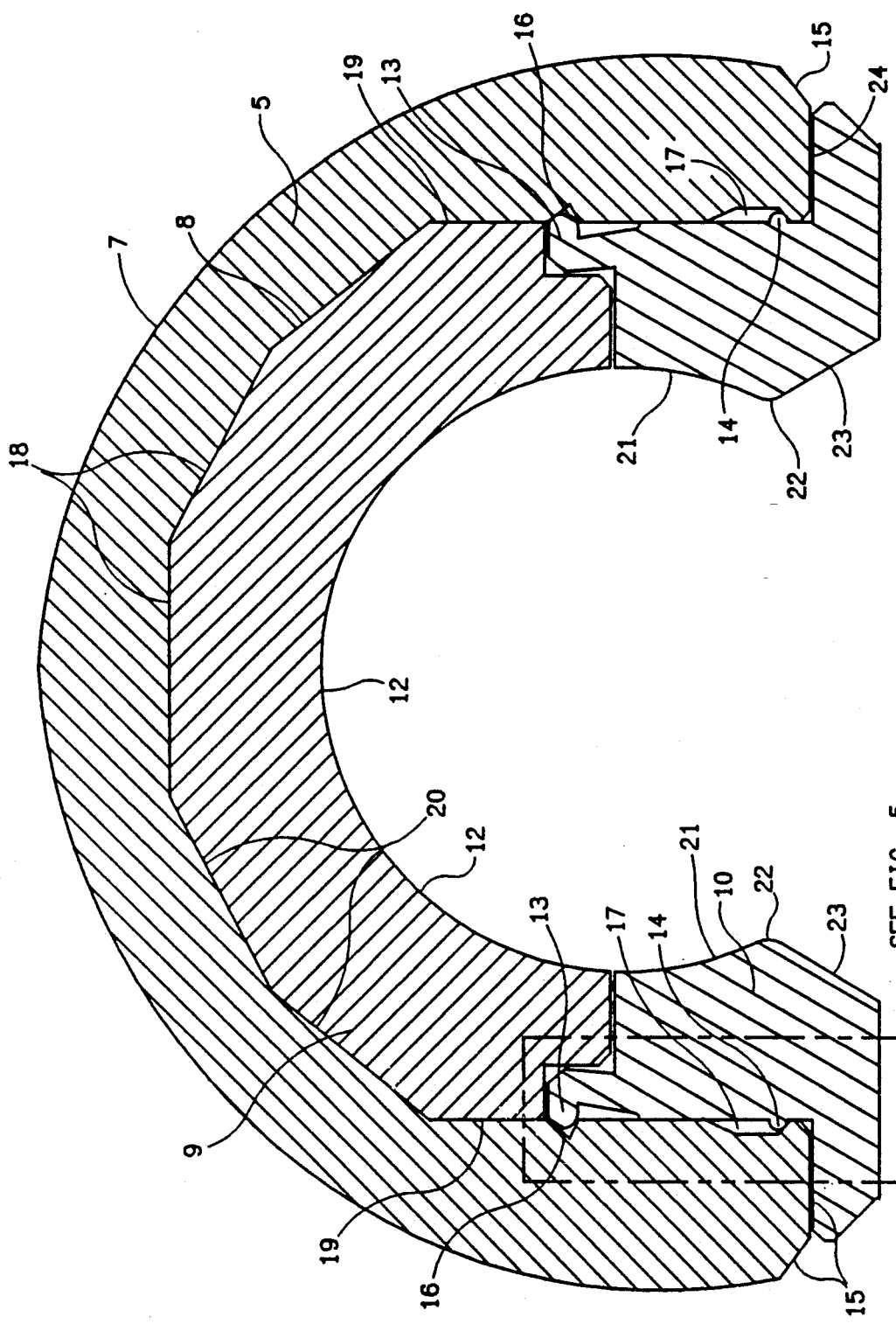
FIG. 4 is a cross-sectional view of a fully assembled bipolar endoprosthesis made in accordance with the preferred embodiment of the present invention.

FIG. 4 is an enlarged cross-sectional side view of a fully assembled and locked bipolar prosthesis embodying the principles of the present invention. The interior 8 of the shell 5 consists of flat planes 18 and vertical side walls 19. The faceted inner surface 8 of the outer shell 5 is made to fit with a correspondingly faceted outer surface 20 of the polyethylene insert 9. The faceted face of the inner surface 8 of the outer shell 5 inhibits rotation of the polyethylene insert 9 and provides for substantial locking integrity of the component assembly. The inner surface 12 of the insert 9, together with the inner surface 21 of the locking ring 10, forms a generally spherical cavity for engaging a femoral head 6. The maximum distance between the throat points 22 is less than the minimum diameter of the femoral head 6. The throat 23 of the bipolar assembly is conically shaped to serve as a guideway for easily receiving an inserted femoral head 6, and to accept contact with the neck of the femoral component 3 during extremes of motion.

Figure 5:
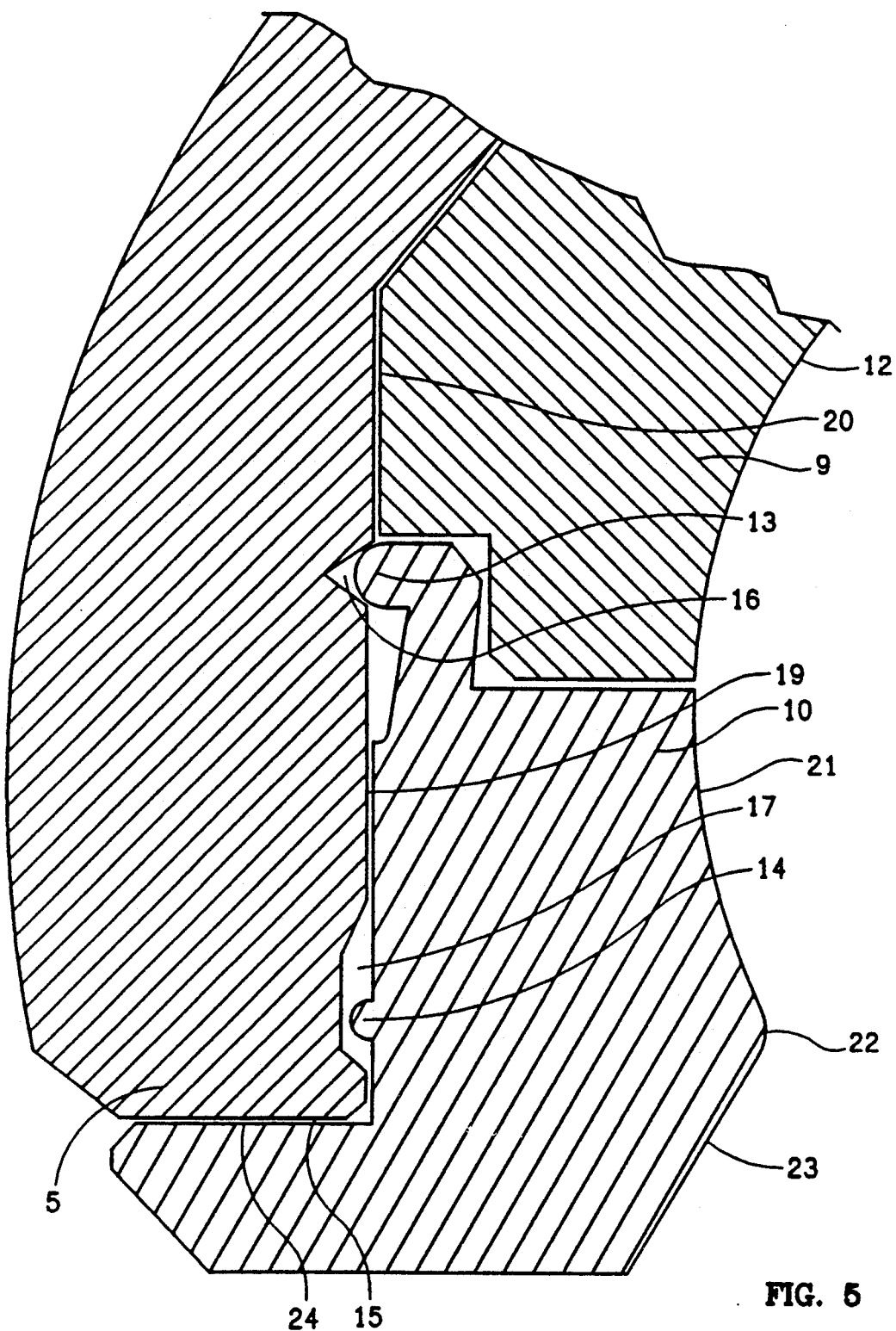
FIG. 5 is a magnified cross-sectional view illustrating the locking mechanism utilized in the preferred embodiment of the present invention.

The locking mechanism of the present invention is shown in FIG. 4 and a magnified view is shown in FIG. 5. The component assembly is locked together by using a system of circumferential barbs (or tabs) and recesses. When the locking ring 10 is snapped into place, the component assembly is securely locked by dual sets of locking barbs 13 and 14. The proximal circumferential barbs 13 are forced into a proximal annular groove 16 recessed into the interior vertical side walls 19 of the outer shell 5. The shape of the proximal barbs 13 acts to provide a preloaded locking interface. The distal circumferential barbs 14 further lock the component into place by engaging a distal annular groove 17 recessed into the throat of the interior side walls 19.

FIGS. 6a, 6b and 6c show plan views of the locking ring 10. As shown in FIG. 6c, the locking ring preferably is segmented into four leaves by four slots 11. As shown in FIG. 6a, the slots 11 are drilled through approximately ¾ the vertical height of the ring 9. This segmentation facilitates the insertion of a femoral prosthesis by enabling throat vertex points 22 to widen via elastic deformation to accept the inserted femoral head 6. Once the femoral head 6 is inserted, the inner surface 21 of the locking ring 10 regains the shape depicted in FIG. 6a. Surface 24 of the locking ring 10 mates with the base 15 of the outer shell 5.

The design of the present invention is well suited to a nesting of internal parts for a particular series of external parts. For example, the outside diameter of outer shell 5 preferably ranges from 43 mm to 61 mm in 1 mm increments. One size of the polyethylene insert 9 can then accommodate outer shells 5 of several different diameters by varying the thickness of the outer shell 5. The inside diameter of the polyethylene insert 9 is nominally 28 mm, but may be of other appropriate diameters (e.g., 22 mm, 26 mm, or 32 mm). By nesting the internal parts in this way, a significant reduction in inventories is achieved producing a cost effective solution.

USE OF THE INVENTIVE STRUCTURE

The inventive device can be installed in several ways. In a first technique, the outer shell 5 is placed into a prepared acetabular socket, and then the insert 9 is placed therein. The locking ring 10 is then inserted into the shell 5 to a first position in which the proximal barbs 13 engage the distal annular groove 17.

In a second technique, the outer shell 5 and the insert 9 are pre-assembled, with the locking ring 10 inserted into the shell 5 to a first position in which the proximal barbs 13 engage the distal annular groove 17.

In both cases, a removable spacer 25 (shown in FIG. 3) that fits around part of the body of the locking ring 10 between the locking barbs 13 and 14 inhibits the ring 10 from being locked into its fully assembled position. In the preferred embodiment, the outer shell 5, insert 9, locking ring 10, and space 25 are preassembled by the manufacturer.

The femoral head 6 (the stem of the femoral component 3 having already been implanted into a femur 4) is then snapped through the center of the locking ring 10 into the assembled components. After the femoral head 6 is in place, the spacer 25 is removed, and the locking ring 10 is pushed deeper into the outer shell 5. In the second case described above, the assembly is then introduced into the acetabulum.

A positive lock of the three subassemblies and the femoral head 6 is achieved when the proximal and distal locking barbs 13, 14 engage the corresponding proximal and distal annular grooves 16, 17 in the interior 8 of the outer metal shell 5.

Although the locking ring 10 provides a substantial locking integrity, it allows for relatively easy intraoperative disassembly. Should the surgeon desire to disassemble the component assembly (for example, in order to select a different size femoral head or replace it with a permanently fixed acetabular component), an osteotome or removal device (not shown) may be wedged into the interface between the surface 24 of the locking ring 10 and the base 15 of the outer shell 15. Sequential levering around the base of the outer shell 15 allows for disassembly. The femoral head or bipolar prosthesis can then be replaced, or a conversion to total hip arthroplasty with a fixed acetabular component can be performed.

SUMMARY

The dual locking mechanism of the present invention provides a major improvement over the prior art. The faceted face of the inner surface 8 of the outer shell 5 inhibits rotation of the polyethylene insert 9 within the shell 5, and thus provides for substantial locking integrity of the component assembly without placing all of the forces on the locking barbs 13, 14. If deformations take place in the interior surface 12 of the insert bearing 9 due to loading from the femoral head 6, the proximal locking barbs 13 would be forced more tightly into the proximal annular groove 16, thus inhibiting disassembly of the component. Additionally, as dislocation of the femoral head 6 from the bipolar device occurs, significant forces would be exerted on the throat 22 of the component. These forces would force the distal locking barbs 14 more deeply into the distal annular groove 17, thus further inhibiting accidental disassembly.

In order for disassembly to occur in vivo, both of these interlocks would have to be defeated. Moreover, there is a tendency for the locking ring 10 to reassemble itself into locking engagement with the outer shell 5. Thus, this configuration provides a bipolar device having substantial locking integrity with a redundant locking mechanism.

A number of embodiments of the present invention have been described. Nevertheless, it will be understood that various modifications may be made without departing from the spirit and scope of the invention. Accordingly, it is to be understood that the invention is not to be limied by the specific illustrated embodiment, but only by the scope of the appended claims.

I claim:

1. A bipolar endoprosthesis adapted to receive a joint prosthesis having a substantially spherical head, comprising:

a. a shell element having a generally hemispherical outer surface and a faceted inner surface, the inner surface having side walls, the side walls having at least two spaced apart annular grooves;

b. a bearing insert element configured to be inserted within the shell element, the insert element having an outer surface shaped to mate with the faceted inner surface and side walls of the shell element to inhibit rotation of the insert element, the inner surface of the insert element having a smooth generally hemispherical shape formed to mate with and allow articulation of the prosthesis spherical head; and c. a removable locking ring configured to lock the insert element into the shell element and to lock the prosthesis head into the insert element, the locking ring having an inner surface formed to mate with and allow articulation of the prosthesis head, the locking ring having an outer surface formed to mate with the shell element inner surface, the locking ring outer surface having at least two sets of longitudinally and circumferentially spaced apart barbs formed to engage the annular grooves in the side walls of the inner surface of the shell element, the joint prosthesis head is removed from the shell element only upon removal of the locking ring.

2. The endoprosthesis of claim 1 wherein the outer surface of the shell element is made of polished metal for placing in a human socket joint.

3. The endoprosthesis of claim 1 wherein the shell element is made of cobalt-chromium-molybdenum metal.

4. The endoprosthesis of claim 1 wherein the bearing insert is formed from a resilient low friction polymer.

5. The endoprosthesis of claim 4 wherein the polymer is medical grade ultra-high molecular weight polyethylene.

6. The endoprosthesis of claim 1 wherein the locking ring is formed from a resilient low friction polymer.

7. The endoprosthesis of claim 6 wherein the polymer is medical grade ultra-high molecular weight polyethylene.

8. The endoprosthesis of claim 1 wherein the joint prosthesis is a femoral component with a spherical femoral head.

9. The endoprosthesis of claim 1 wherein the locking ring is segmented by at least two vertical slots to allow for relatively easy insertion of the prosthesis spherical head.

10. The endoprosthesis of claim 1 wherein the locking ring has a base having a conically shaped guideway shaped to guide the spherical head into the endoprosthesis.

11. The endoprosthesis of claim 10 wherein a maximum diameter of the guideway is less than a minimum diameter of the spherical head.

12. The endoprosthesis of claim 1 wherein the bearing insert element is symmetrical.

13. The endoprosthesis of claim 1 wherein the endoprosthesis is configured such that the joint prosthesis head is inserted into the locking ring only before the locking ring is inserted into the shell element.

14. The endoprosthesis of claim 1 wherein the locking ring is locked into the shell element through a friction fit.

* * * * *